(12) United States Patent
Schnappinger

(10) Patent No.: US 8,568,796 B2
(45) Date of Patent: Oct. 29, 2013

(54) PHARMACEUTICAL COMPOSITION AND METHOD FOR REDUCING WEIGHT

(76) Inventor: Uta Schnappinger, Loxstedt (DE)

(*) Notice: Subject to any disclaimer, the term of this patent is extended or adjusted under 35 U.S.C. 154(b) by 0 days.

(21) Appl. No.: 13/185,590

(22) Filed: Jul. 19, 2011

(65) Prior Publication Data

US 2013/0022690 A1    Jan. 24, 2013

(51) Int. Cl.
*A61K 33/10*    (2006.01)
(52) U.S. Cl.
USPC ........... 424/725; 424/687; 424/760; 424/400; 426/648
(58) Field of Classification Search
None
See application file for complete search history.

(56) References Cited

PUBLICATIONS

German website gofeminin.de forum entry "Fuculacca . . . doch Nebenwirklungen and Gegananzeigen," 2003 http://forum.gofeminin.de/forum/fitness3/__f1221__fitness3-Fuculacca-doch-Nebenwirklungen-und-Gegenanzeigen.html.*

\* cited by examiner

*Primary Examiner* — Kortney L Klinkel
*Assistant Examiner* — Alissa Prosser
(74) *Attorney, Agent, or Firm* — Stephan A. Pendorf; Patent Central LLC

(57) ABSTRACT

A pharmaceutical composition, particularly homeopathic medicines for weight reduction, including the following components: *Adonis vernalis*, Calcium carbonicum Hahnemann, Capsicum, Cascara, *Fucus vesiculosus*, Graphites and Kalium Carbonicum and *Phytolacca*, as well as a nutrition and a method for weight reduction.

6 Claims, No Drawings

PHARMACEUTICAL COMPOSITION AND METHOD FOR REDUCING WEIGHT

TECHNICAL FIELD OF THE INVENTION

The present invention relates to a pharmaceutical composition, particularly homeopathic medicines for weight reduction, comprising the following components: *Adonis vernalis*, Calcium carbonicum Hahnemann (calcium carbonate), Capsicum, Cascara (e.g. *Rhamnus purshiana*), *Fucus vesiculosus*, Graphites (graphite) and Kalium Carbonicum (potassium carbonate) and *Phytolacca* (American Pokeweed (*Phytolacca americana*)). In addition the invention relates to a nutrition and a method for weight reduction.

Homeopathy is a form of alternative medicine. Practitioners or Homeopaths treat patients using highly diluted preparations that cause healthy people to exhibit symptoms that are similar to those exhibited by the patient to be treated finally. In the context of homeopathy, the term remedy is used to refer to a substance which has been prepared with a particular procedure and intended for patient use.

The basic principle of homeopathy, known as the "law of similars", is "let like be cured by like." It was first stated by German physician Samuel Hahnemann in 1796. Homeopathic remedies are prepared by serial dilution with shaking by forceful striking on an elastic body, which homeopaths term succussion. Each dilution followed by succussion is assumed to increase the effectiveness. This process is called potentiation.

Dilution often continues until none of the original substance remains. Apart from the symptoms, homeopaths examine aspects of the patient's physical and psychological state, then homeopathic reference books known as repertories are consulted, and a remedy is selected based on the totality of symptoms.

In the prior art various pharmaceutical drugs, compositions and homeopathic medicines are well known to produce different effects. It is known that pharmaceuticals, particularly homeopathic medicines, help to support the reduction of body weight. The well-known homeopathic medicines have several homeopathic active ingredients. These homeopathic active ingredients may occur in different potencies and dilutions (Dil.), for example: D1 equals 1 part of the original substance in 10 parts of the solution, D2 equals 1 part of the original substance in 100 parts of the solution, D3 equals 1 part of the original substance in 1,000 parts of the solution, D6 equals 1 part of the original substance in 1 million parts of the solution, D9 equals 1 part of the original substance in 1 billion parts of the solution, D12 equals 1 part of the original substance in 1 trillion parts of the solution, D20 equals 1 part of the original substance in 100 quintillion parts of the solution, D23 equals 1 part of the original substance in 100 sextillion parts of the solution.

Homeopathy involves a process known by practitioners as "dynamisation" or "potentiation" whereby a substance is diluted with alcohol or distilled water and then vigorously shaken in a process called "succussion". The founder of homeopathy, Samuel Hahnemann believed that the process of succussion activated the "vital energy" of the diluted substance, and that successive dilutions increased the "potency" of the remedy.

The Homeopathic Pharmacopoeia, in German "homoopathische Arzneibuch (HAB)" is similar to other pharmaceutical books and includes a general part and a part with monographs of the starting substances, in addition to their usual quality standards and specifications.

Several potency scales are in use in homeopathy. Homeopaths developed a decimal scale (D or Dil.), diluting the substance to ten times its original volume each stage. Serial dilution of a solution results, after each dilution step, in fewer molecules of the original substance per liter of solution. Homeopaths maintain that this water retains some "essential property" of the original material, because the preparation has been shaken after each dilution. It is believed that the dynamisation or shaking of the solution caused a healing force, released from the substances. Even though the homeopathic remedies are often extremely diluted, homeopaths maintain that a healing force is retained by these homeopathic preparations.

AIM OF THE PRESENT INVENTION

The aim of the present invention is to provide a pharmaceutical composition, in particular homeopathic medicines, which helps a patient to reduce his or her body weight and to stabilize his or her weight at a lower level for a long time without suffering the yo-yo effect after having lost body weight.

Another aim of the present invention is to achieve a significantly higher efficiency in the body weight reduction. During the body weight reduction, the homeopathic medicines should introduce and maintain a sense of well-being and happiness to the patient.

Another aim of the present invention is to provide a non-alcoholic liquid solvent for body weight reduction.

A further aim of the present invention is to provide a method of manufacturing a pharmaceutical composition for increasing the effectiveness of the pharmaceutical composition.

Another aim of the present invention is to provide a method for weight reduction.

Another aim of the present invention is to provide a secure and self administrable method of weight reduction.

A further aim of the present invention is to provide a method for weight reduction wherein a defined amount of a pharmaceutical composition is administered.

Another aim of the present invention is to provide a method for weight reduction, wherein the effectiveness of the method is increased.

SUMMARY OF THE INVENTION

In one aspect the present invention provides a pharmaceutical composition, particularly homeopathic medicines for weight reduction, with the following elements and components and the respective potencies and dilutions, namely *Adonis vernalis*, in D2 up to D9 Dil., Calcium carbonicum Hahnemann, in D8 up to D24 Dil., Capsicum, in D2 up to D9 Dil., Cascara, in D2 up to D9 Dil., *Fucus vesiculosus*, in D1 up to D9 Dil., Graphites, in D8 up to D24 Dil., Kalium Carbonicum (potassium carbonate), in D4 up to D12 Dil. and *Phytolacca*, in D2 up to D9 Dil.

It is the first time ever that it is possible to support a reduction of the weight or reduce the body weight, while keeping the reduced body weight over a long time and not suffering the yo-yo-effect. In particular, all body functions are affected and increased. The body's fat burning process is boosted by means of natural plant-based supports. The detoxification of the body is boosted and the formation of endorphins is stimulated. Especially the emotional hunger is suppressed, so no feeding frenzy is coming up to the patient.

The pharmaceutical composition stimulates the body's central regulating mechanisms. As a result, metabolism is activated and increased, so that the body uses more energy despite low calorie intake. This energy comes from nothing other than the fat depots of the body.

The pharmaceutical composition particularly preferably features only the following medically active ingredients in the given potencies and amount:

1 part Adonis vernalis D6 Dil.,
1 part Calcium carbonicum Hahnemann D15 Dil.,
1 part Capsicum D6 Dil.,
1 part Cascara D5 Dil.,
1 part Fucus vesiculosus D4 Dil.,
2 parts Fucus vesiculosus D6 Dil.,
1 part Graphites D15 Dil.,
1 part Kalium Carbonicum D8 Dil. and
1 part *Phytolacca* D5 Dil.

By use of this combination of active ingredients, the patient gets through the process of body weight reduction easily, especially in combination with the right nutrients. A yo-yo effect is effectively prevented by this pharmaceutical composition. The metabolism is increased and the fat-burning process is running at full speed. As an additional effect the health is returning. Other benefits are for example no hunger pangs, "good mood" because the patient's mind is at ease, a boosted self-esteem. No negative side effects of any kind are registered in clinical tests, but for all patients an improved health is determined.

The components of the pharmaceutical composition are potentiated in common in the last or in the last two potencies. In particular, the effect is enhanced by the joint potentiating in the last or the last two dilution-steps. For Example different substances are potentiated alone until each one has reached a dilution for example D6, then they are put together and are diluted/potentiated jointly/in common one more time for example to the dilution D7. So the components have been diluted/potentiated in common in the last step.

If the pharmaceutical composition is exclusively present as an aqueous solution, the complete absence of alcohol as a diluent and/or a carrier medium is assured. There will be no alcoholic basis for this pharmaceutical composition.

Another aspect of the invention is to provide a method for reducing the body weight by administering the pharmaceutical composition according to claim 1 or 2. Hereby the body weight can be reduced in a very high effective way. A female patient is able to reduce her weight by approximately 13 to 18 lbs. (6 to 8 kilogram) in four weeks. A male patient is able to reduce his body weight by approximately 22 to 27 lbs. (10 to 12 kilogram) in four weeks.

The time expended for the treatment with the pharmaceutical composition can be reduced to a minimum because the pharmaceutical composition is self administered by the patient by using a special applicator (German Trademark ADAPPLICATOR).

The self-administering is done by the patient with a needle-free trans-mucosal applicator for injecting solvings into the mouth of the patient so that no needles or counting beads or droplets is needed. The needle-free trans-mucosal applicator for injecting solvings into the mouth of the patient is used three times a day with an exact defined doses of 0.0304 fl oz (0.09 ml) spray volume per stroke so the patient can not be administered with a wrong dosage.

The whole Method is exclusively carried out by professionally trained doctors or alternative practitioners and comprises only two stages: Stage 1—Weight loss, Stage 2—Stabilization.

In Stage 1 (Weight Loss) the initial counseling session is used to determine how much weight the patient wants to lose. The patient is being weighed and measured. After this a nutrition plan is given to the patient. This nutrition plan is easy to follow in every situation. Three times a week a meeting between the patient and an consulting will be held, in which the weight of the patient is controlled.

The patient is given an exact calculated nutrition plan including the right nutrients in the correct amount, for example protein in the form of fresh meat, carbohydrates in the form of fresh vegetables, salad and fruits. No fat is added to the nutrition, because the body is using the fat reserves. Additionally vital substances and water is served in the nutrition plan.

The Nutrition for the patient is adapted, balanced and accurately calculated to the body composition and body weight of the patient. The nutrition only consists of proteins, carbohydrates, vital substances like vitamins and minerals and the like and water.

In a preferred embodiment the nutrition consists of 22 percent proteins, 1 percent carbohydrates, 6 percent vital substances and 70 percent water.

Stage 2 (Stabilization) begins after having reached the desired weight. In this stage the patient is advised by his personal consultant how he or she recognizes and manages his or her personal food limits. The patient learns how to maintain his or her weight with new eating habits. The administering of the pharmaceutical composition is continued, so every patient receives a continued application of the pharmaceutical composition for only four weeks after having reached the designated body weight. In Stage 2 the dose of the pharmaceutical composition is reduced to one application a week.

After having accomplished stage 2, which includes a minimum and perfect time of four weeks of stabilization, a third stage is possible to take part in. The patient may participate in follow-up sessions as long as needed. For best results a meeting consideration should be held once a month for six months to check the patients weight.

It is also possible to lose even more weight and restart treatment, simply because feeling great, physically and mentally. The best way to keep this high level of health is to repeat the treatment at regular intervals, for example every spring or fall.

The invention claimed is:

1. A pharmaceutical composition of which the medically active components consist essentially of the following with the respective dilutions:

1 part *Adonis vernalis* D6 Dil.,
1 part Calcium carbonicum Hahnemann D15 Dil.,
1 part Capsicum D6 Dil.,
1 part Cascara D5 Dil.,
1 part *Fucus vesiculosus* D4 Dil.,
2 parts *Fucus vesiculosus* D6 Dil.,
1 part Graphites D15 Dil.,
1 part Kalium Carbonicum D8 Dil. and
1 part *Phytolacca* D5 Dil.

2. The pharmaceutical composition according to claim 1, wherein the pharmaceutical composition is present as an alcohol-free aqueous liquid solution.

3. The pharmaceutical composition according to claim 1, wherein the pharmaceutical composition is present as an aqueous liquid solution.

4. A pharmaceutical composition of which the medically active components consist of the following with the respective dilutions:

1 part *Adonis vernalis* D6 Dil.,
1 part Calcium carbonicum Hahnemann D15 Dil.,
1 part Capsicum D6 Dil.,
1 part Cascara D5 Dil.,
1 part *Fucus vesiculosus* D4 Dil., 2 parts *Fucus vesiculosus* D6 Dil.,
1 part Graphites D15 Dil.,
1 part Kalium Carbonicum D8 Dil. and
1 part *Phytolacca* D5 Dil.

5. A method of manufacturing the pharmaceutical composition according to claim 1, comprising diluting the medically active ingredients in an aqueous medium in one or more steps, wherein a joint dilution of all components is carried out in the last dilution.

6. A method of manufacturing the pharmaceutical composition according to claim 1, comprising diluting the medically active ingredients in an aqueous medium in more than one step, wherein a joint dilution of all components is carried out in the last two dilutions.

\* \* \* \* \*